US008751196B2

(12) United States Patent
Moriya et al.

(10) Patent No.: US 8,751,196 B2
(45) Date of Patent: Jun. 10, 2014

(54) ABNORMALITY DETECTION SYSTEM, ABNORMALITY DETECTION METHOD, RECORDING MEDIUM, AND SUBSTRATE PROCESSING APPARATUS

(75) Inventors: Tsuyoshi Moriya, Tokyo (JP); Yasutoshi Umehara, Sapporo (JP); Yuki Kataoka, Sapporo (JP); Michiko Nakaya, Nirasaki (JP)

(73) Assignee: Tokyo Electron Limited, Tokyo (JP)

( * ) Notice: Subject to any disclaimer, the term of this patent is extended or adjusted under 35 U.S.C. 154(b) by 321 days.

(21) Appl. No.: 13/381,367

(22) PCT Filed: Jun. 28, 2010

(86) PCT No.: PCT/JP2010/060957
§ 371 (c)(1),
(2), (4) Date: Jan. 10, 2012

(87) PCT Pub. No.: WO2011/001929
PCT Pub. Date: Jan. 6, 2011

(65) Prior Publication Data
US 2012/0109582 A1    May 3, 2012

(30) Foreign Application Priority Data
Jun. 30, 2009    (JP) .................................. 2009-155370

(51) Int. Cl.
G06F 15/00    (2006.01)
G01N 29/44    (2006.01)

(52) U.S. Cl.
USPC ............................................ 702/183; 702/81

(58) Field of Classification Search
USPC ............ 702/39, 48, 56, 81, 84, 183; 700/109, 700/121
See application file for complete search history.

(56) References Cited

U.S. PATENT DOCUMENTS 7,974,067 B2 * 7/2011 Ito et al. ......................... 361/234
8,082,124 B2 * 12/2011 Miyano et al. ................. 702/183
2006/0100824 A1 5/2006 Moriya
2012/0186745 A1 * 7/2012 Miya et al. ............... 156/345.27

FOREIGN PATENT DOCUMENTS

| JP | 2003-100714 A | 4/2003 |
| JP | 2003-173896 A | 6/2003 |
| JP | 2004-319857 A | 11/2004 |
| JP | 2006-128304 A | 5/2006 |
| JP | 2008-042005 A | 2/2008 |

OTHER PUBLICATIONS

International Search Report issued on Sep. 28, 2010 for WO2011/001929 A1 and English translation thereof.

* cited by examiner

Primary Examiner — Manuel L Barbee
(74) Attorney, Agent, or Firm — Abelman, Frayne & Schwab

(57) ABSTRACT

Disclosed is an abnormality detection system that accurately detects abnormalities that arise in a device. The abnormality detection system 100, which detects abnormalities that arise in a plasma processing device 2, is provided with: a plurality of ultrasonic sensors 41, which detects acoustic emissions (AE), which cause abnormalities to arise; a distributor 65, which distributes each output signal from the ultrasonic sensors 41 into a first signal and a second signal; a trigger 52, which samples the first signal at, for example, 10 kHz, and generates a trigger signal when predetermined characteristics are detected; a trigger generation time counter 54, which receives trigger signals and determines the time of trigger generation; a data logger board 55, which creates sampling data from sampling the second signal at, for example, 1 MHz; and a PC 50, which analyzes abnormalities arising in the plasma processing device 2 by means of performing a waveform analysis of data from the sampling data, said data corresponding to a set time period using the time of trigger generation determined by the trigger generation time counter 54 as a benchmark.

15 Claims, 9 Drawing Sheets

ABNORMALITY DETECTION SYSTEM, ABNORMALITY DETECTION METHOD, RECORDING MEDIUM, AND SUBSTRATE PROCESSING APPARATUS

CROSS REFERENCE TO RELATED APPLICATIONS

This application is a national phase of PCT application No. PCT/JP2010/060957, filed 28 Jun. 2010, which claims priority to JP patent application No. 2009-155370, filed 30 Jun. 2009, all of which are incorporated herein by reference.

TECHNICAL FIELD

The present invention relates to an abnormality detection system, an abnormality detection method by the abnormality detection system, a computer-readable recording medium storing a program used in the abnormality detection system, and a substrate processing apparatus.

BACKGROUND ART

A plasma processing apparatus for performing predetermined plasma processing on a semiconductor wafer or a substrate such as a flat display panel commonly includes an accommodating chamber (hereinafter, referred to as a "chamber") that accommodates a substrate. In such a substrate processing apparatus, high-frequency power is applied to the chamber while the processing gas flows into the chamber, such that plasma is generated from the processing gas, thereby performing the plasma processing on the substrate by the generated plasma.

When the high-frequency power is applied to the chamber, there are some cases where abnormality such as plasma abnormal discharge (for example, micro-arching) occurs due to various factors. The plasma abnormal discharge generates a crack or a notch on the substrate surface, or damages constituent components disposed in the chamber by a fire, and also generates particles by releasing deposits attached to the constituent components (for example, upper electrode) in the chamber.

For that reason, it is necessary to detect the plasma abnormal discharge in early stage, such that, when the plasma abnormal discharge is detected, appropriate countermeasures, for example, to stop an operation of the plasma processing apparatus are rapidly performed, thereby preventing the damage to the substrate or constituent components and the generation of the particles. Accordingly, various methods for detecting the abnormality such as the plasma abnormal discharge or the like in early stage have been developed.

For example, as a method capable of performing high-sensitive detection of the plasma processing method, a method for detecting an acoustic emission (AE) caused by energy discharge in the plasma abnormal discharge has been considered. As a detection apparatus using the AE, detection apparatuses is known, in which a plurality of ultrasonic sensors are disposed on an outer wall of a chamber, and the ultrasonic sensors detect the AE caused by energy discharge when the plasma abnormal discharge occurs, or in which a plurality of acoustic probes are installed so as to be in contact with a loading plate (susceptor) that loads a semiconductor wafer, or a focus ring disposed around the semiconductor wafer loaded on the loading plate, and an ultrasonic wave propagating the acoustic probes is detected by the ultrasonic sensor (for example, see Patent Document 1). In this case, a method for monitoring high-frequency power (voltage or current) used for generation of the plasma may be used in combination.

PRIOR DOCUMENT

Patent Document 1: Japanese Patent Application Laid-Open No. 2003-100714

SUMMARY OF INVENTION

Problems to be Solved by the Invention

However, the ultrasonic sensor not only detects the AE caused by the plasma abnormal discharge but also detects a mechanical vibration caused by opening and closing of a gate valve of the plasma processing apparatus as noise. Accordingly, there is a problem in that the degree of precision for the detection of the plasma abnormal discharge deteriorates. In order to solve the problem, improvement in an analysis method of the AE signal detected by the ultrasonic sensor is required.

As the analysis method of the AE signal, there is, for example, a method which includes sampling an output signal (detected signal) of the ultrasonic sensor at high speed, and digital-processing the acquired data on a personal computer (PC). However, since the method needs to handle large-capacity data due to the high-speed sampling, there are problems in that data processing costs increase and the data cannot be processed in real time.

A method for digital-processing the data by using in combination with mock-up is also used, but the method is merely to correspond to the sampling at 10 kHz because of a limit of a processing capacity of a digital signal processor (DSP). The sampling frequency is enough to monitor the high-frequency power, but is not enough to monitor the AE signal caused by the abnormality of about a micro-second in a time from the start of the occurrence to the end.

However, in the related art, although a plurality of ultrasonic sensors are disposed, the analysis of the AE signal is performed by each of the ultrasonic sensors. In this case, for example, since a size of the AE signal is different due to a difference in an occurrence portion of the plasma abnormal discharge, there is a problem in that the occurrence of the plasma abnormal discharge may not be detected.

The object of the present invention is to provide an abnormality detection system, an abnormality detection method by the abnormality detection system, a computer-readable recording medium storing a program used in the abnormality detection system that can acquire large-capacity data on abnormality occurring in a processing apparatus while reducing data processing costs, and detect the occurring abnormality with high precision, and a substrate processing apparatus.

Means for Solving the Problems

In order to achieve the above object, the abnormality detection system according to the present invention is an abnormality detection system for detecting abnormality occurring in a processing apparatus in which AE as noise ma be mixed into AE generated from an abnormality detection target, characterized by including: a plurality of ultrasonic sensors for detecting acoustic emission generated in the processing apparatus; a distributing unit configured to distribute each output signal of the plurality of ultrasonic sensors to a first signal and a second signal; a trigger generating unit configured to generate a trigger signal when a predetermined feature is detected by sampling the first signal at a first frequency; a trigger generation time determining unit configured to determine a trigger generation time by receiving the trigger signal; a data making unit configured to make sampling data by sampling the second signal at a second frequency higher than the first frequency; and a data processing unit configured to analyze the abnormality generated in the processing apparatus by performing a waveform analysis of data corresponding to a predetermined period based on the trigger generation time determined by the trigger generation time determining unit among the sampling data.

In addition, the abnormality detection system may further include a trigger signal processing unit configured to integrate the plurality of trigger signals into one signal as a representative trigger signal when the plurality of trigger signals are generated within a predetermined period, in which the trigger generation time determining unit may determine the trigger generation time for the representative trigger signal.

In addition, the abnormality detection system may further include a filter configured to remove noise from each output signal of the plurality of ultrasonic sensors.

Further, in the abnormality detection system, the first frequency may be 10 kHz to 5 MHz, and the second frequency may be 500 kHz to 5 MHz.

In order to achieve the above object, the abnormality detection method according to the present invention is an abnormality detection method for detecting abnormality occurring in a processing apparatus in which AE as noise may be mixed into AE generated from an abnormality detection target, characterized by including steps of: detecting acoustic emission generated in the processing apparatus by a plurality of ultrasonic sensors; distributing each output signal from the plurality of ultrasonic sensors which is acquired in the step of detecting to a first signal and a second signal by a distributing unit; generating a trigger signal by a signal generating unit when a predetermined feature is detected by sampling the first signal at a first frequency by an A/D conversion unit; determining a trigger generation time of the trigger signal by a time counter unit by receiving the trigger signal; making sampling data by sampling the second signal at a second frequency higher than the first frequency by the A/D conversion unit; and processing data of analyzing the abnormality generated in the processing apparatus by performing a waveform analysis of data corresponding to a predetermined period by a computer based on the trigger generation time determined in the step of determining a trigger generation time among the sampling data.

In addition, the abnormality detection method according to the present invention may further include a step of processing a trigger signal of integrating the plurality of trigger signals into one signal as a representative trigger signal when the plurality of trigger signals are generated within a predetermined period in the generating of the trigger signal, in which in the step of determining a trigger generation time, the trigger generation time may be determined for the representative trigger signal.

In addition, the abnormality detection method according to the present invention may further include a step of removing noise from the first signal and the second signal acquired in the step of distributing by a filter.

Further, in the abnormality detection method according to the present invention, the first frequency may be 10 kHz to 5 MHz, and the second frequency may be 500 kHz to 5 MHz.

Further, in the abnormality detection method according to the present invention, the step of processing data may further include steps of: cutting the data that correspond to the predetermined period from the sampling data; a first extracting of extracting a waveform feature quantity from down sampling data when a meaningful waveform exists in a made down sampling data by performing down sampling according to a representative value with respect to the data cut in the data cutting step; a second extracting of extracting a waveform feature quantity from the data cut in the data cutting step with respect to an analysis target by estimating a time of the waveform feature quantity extracted in the step of the first extracting to narrow the analysis target of the data cut in the step of cutting step; and judging the abnormality occurring in the processing apparatus by performing pattern recognition between the waveform feature quantity acquired in the step of the second extracting and a predetermined abnormal pattern recognition model.

In addition, the abnormality detection method according to any one of claims 5 through 9 of the present invention, further includes a step of acquiring a process condition of predetermined processing executed in the processing apparatus performed before the step of detecting, in which the step of detecting may be performed only for an executing period of the predetermined processing included in the process condition acquired in the step of acquiring a process condition.

In order to achieve the above object, the computer-readable recording medium according to the present invention is a computer-readable recording medium for storing a program for executing an abnormality detection method for detecting the abnormality occurring in a processing apparatus, in which AE as noise ma be mixed into AE generated from an abnormality detection target, determined as an abnormality detection system controlled by a computer, in which the abnormality detection method includes steps of: detecting acoustic emission generated in the processing apparatus by a plurality of ultrasonic sensors; distributing each output signal from the plurality of ultrasonic sensors which is acquired in the step of detecting to a first signal and a second signal by a distributing unit; generating a trigger signal by a signal generating unit when a predetermined feature is detected by sampling the first signal at a first frequency by an A/D conversion unit; determining a trigger generation time of the trigger signal by a time counter unit by receiving the trigger signal; making sampling data by sampling the second signal at a second frequency higher than the first frequency by the A/D conversion unit; and processing data of analyzing the abnormality generated in the processing apparatus by performing a waveform analysis of data corresponding to a predetermined period by a computer based on the trigger generation time determined in the step of determining a trigger generation time among the sampling data.

In the above-described abnormality detection system, the processing apparatus may be a processing apparatus for semiconductor wafers or glass substrates.

In the above-described abnormality detection system, the processing apparatus may be any one of an etching apparatus, a CVD film forming apparatus, an ashing apparatus, a coating and developing apparatus, a substrate cleaning apparatus, and a thermal processing apparatus.

In the above-described abnormality detection system, the substrate processing apparatus may be a plasma processing apparatus.

In order to achieve the object, the substrate processing apparatus may include the above-described abnormality detection system.

According to the abnormality detection system of the present invention, the abnormality detection method as defined in claim 5 and computer-readable recording medium as defined in claim 11, it is possible to acquire large-capacity data on abnormality occurring in a processing apparatus while reducing data processing costs, and detect the occurring abnormality with high precision.

According to the abnormality detection system of the present invention and the abnormality detection method as defined in claim 6, it is possible to reduce a load on the data processing without deteriorating the precision of the abnormality detection, by generating a representative trigger signal.

Further, according to the abnormality detection method of the present invention, it is possible to improve analysis precision in the generation of the trigger signal or the sampling data because noises are removed from each output signal of the ultrasonic sensor by the filter.

Further, according to the abnormality detection system and the abnormality detection method of the present invention, it is possible to detect all AE signals due to the abnormality, which is difficult to be detected by a conventional method which ends at about micro-second after the occurrence.

Further, according to the abnormality detection method of the present invention, it is possible to reduce data processing time without deteriorating the precision of the abnormality detection by using down sampling data having a small data quantity after decreasing the data quantity that is an analytic processing target by the data cutting and narrowing the analytic processing target.

Further, according to the abnormality detection method of the present invention, it is possible to reduce a load on the entire data processing and perform an analysis and judgment by narrowing kinds of the detected abnormality because the data in the detecting is acquired only for an executing period of the predetermined processing included in the process condition.

MODE FOR CARRYING OUT THE INVENTION

Hereinafter, exemplary embodiments of the present invention will be described with reference to the accompanying drawings.

Figure 1:
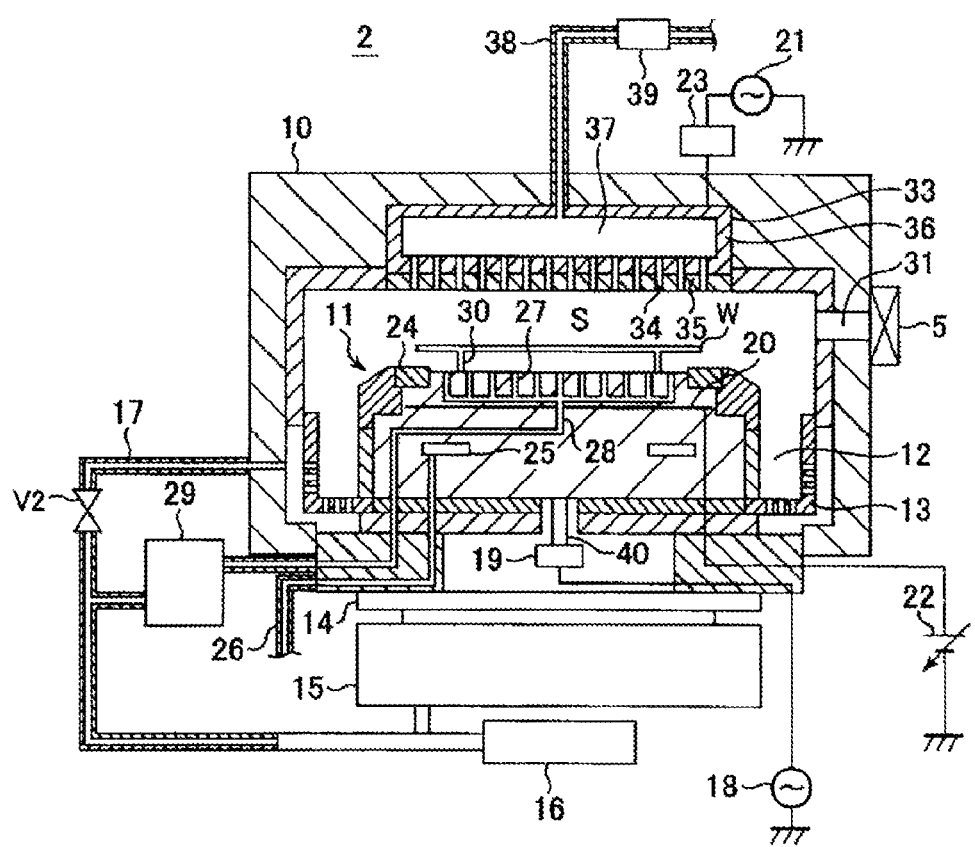
FIG. 1 is a cross-sectional view showing a schematic configuration of a plasma processing apparatus applied with an abnormality detection system according to the present invention.

FIG. 1 is a cross-sectional view showing a schematic configuration of a plasma processing apparatus applied with an abnormality system according to an exemplary embodiment of the present invention. A plasma processing apparatus 2 performs an etching processing on a semiconductor wafer (hereinafter, referred to as a "wafer") W and includes a cylindrical chamber 10 made of metal such as aluminum or stainless steel and a cylindrical susceptor 11 as a stage loading wafer W having, for example, a diameter of 300 mm is included in chamber 10.

Chamber 10 includes an opening (not shown) for maintenance which is communicated with the inside and the outside of chamber 10, and a cover (not shown) for maintenance which freely opens and closes the opening. A ventilation channel 12 functioning as a flow channel for discharging gas above susceptor 11 out of chamber 10 is installed between the side wall of chamber 10 and susceptor 11. A circular vent plate 13 is disposed in the middle of ventilation channel 12 and a space lower than vent plate 13 is communicated with an adaptive pressure control valve (APC) 14 as a variable butterfly valve. APC 14 is connected to a turbo molecular pump (TMP) 15 as a vent pump for vacuum operation and TMP 15 is connected to a dry pump (DP) 16 as a vent pump.

Meanwhile, the ventilation channel configured by APC 14, TMP 15, and DP 16 is hereinafter called a "main vent line". In the main vent line, a pressure control in chamber 10 is performed by APC 14 and decompression in chamber 10 in a vacuum state may be performed by TMP 15 and DP 16.

The space lower than vent plate 13 is communicated with DP 16 through a separate ventilation channel (hereinafter, referred to as a "roughing line") different from the main vent line. The roughing line includes, for example, a vent pipe 17 having a diameter of 25 mm and a valve V2 disposed in the middle of vent pipe 17, and the gas in chamber 10 may be discharged by passing through the roughing line when driving DP 16.

A high-frequency power supply 18 supplying predetermined high-frequency power to susceptor 11 through a power supply rod 40 and a matching unit 19 is connected to susceptor 11. As a result, susceptor 11 serves as a lower electrode. In addition, matching unit 19 reduces reflection of the high-frequency power from susceptor 11 to improve supply efficiency of the high-frequency power to susceptor 11. Meanwhile, the power outputted from high-frequency power supply 18 is monitored by a current sensor or a voltage sensor (not shown).

A disk electrode plate 20 including a conductive film is disposed at the inner-upper side of the susceptor 11 in order to adsorb wafer W by an electrostatic adsorption force and a DC power supply 22 is electrically connected to electrode plate 20. Wafer W is adsorbed and held on the upper surface of susceptor 11 by a Coulomb's force or a Johnsen-Rahbek force which is generated by DC voltage applied to electrode plate 30 from DC power supply 22. In order to converge the plasma generated from an upper space S of susceptor 11 toward wafer W, an annular focus ring 24 made of silicon (Si) and the like is disposed at the upper side of susceptor 11.

A refrigerant chamber 25 is disposed in susceptor 11 and refrigerant chamber 25 has a ring shape extending in a circumferential direction. Refrigerant (for example, cooling water) having a predetermined temperature is circulated and supplied to refrigerant chamber 25 from a chiller unit (not shown) through a pipe 26, such that a processing temperature of wafer W disposed on susceptor 11 is controlled according to the temperature of the refrigerant.

A plurality of heating gas supplying holes 27 and heating gas supplying grooves (not shown) are formed at a portion (hereinafter, referred to as an "adsorption surface") in which wafer W is adsorbed in the upper surface of susceptor 11. Heating gas supplying holes 27 are connected to a heating gas supplying unit 29 through a heating gas supplying line 28 installed in susceptor 11, and heating gas supplying unit 29 supplies the heating gas such as He gas to a gap between the adsorption surface and the rear surface of wafer W. Meanwhile, heating gas supplying unit 29 is connected to DP 16 so as to make the gap between the adsorption surface and the rear surface of wafer W into a vacuum.

A plurality of pusher pins 30 as lift pins which freely protrude from the upper surface of susceptor 11 are disposed at the adsorption surface of susceptor 11. Pusher pins 30 are movable in a vertical direction of FIG. 1 by converting a rotary motion of a motor (not shown) into a straight-line motion by a ball thread and the like. When wafer W is adsorbed and held on the adsorption surface, pusher pins 30 are housed in susceptor 11, and when wafer W is carried in or out chamber 10, pusher pins 30 protrude from the upper surface of susceptor 11 to lift up wafer W spaced apart from susceptor 11.

A shower head 33 is disposed at a ceiling part of chamber 10. A high-frequency power 21 is connected to shower head 33 through a matching unit 23 and high-frequency power 21 supplies the predetermined high-frequency power to shower head 33. As a result, shower head 33 serves as an upper electrode. Meanwhile, the function of matching unit 23 is the same as the function of matching unit 19 described above.

Further, the power outputted from high-frequency power supply 21 is monitored by a current sensor or a voltage sensor (not shown).

Shower head 33 includes an electrode plate 35 disposed at the bottom of shower head 33 and having a plurality of gas vent holes 34 and an electrode support 36 detachably supporting electrode plate 35. Further, a buffer chamber 37 is installed in electrode support 36, and buffer chamber 37 and a processing gas supplying unit (not shown) are connected with each other by a processing gas injection duct (pipe) 38. A pipe insulator 39 is disposed in the middle of processing gas injection duct 38, and pipe insulator 39 includes an insulator and prevents the high-frequency power supplied to shower head 33 from flowing into the processing gas supplying unit through processing gas injection duct 38.

A gate valve 5 opening and closing a carrying in/out port 31 of wafer W is attached to the side wall of chamber 10.

In plasma processing apparatus 2, high-density plasma including ions or radicals is generated in space S by supplying the high-frequency power to susceptor 11 and shower head 33 and supplying the processing gas from shower head 33 to space S between susceptor 11 and shower head 33.

When the etching processing is performed in plasma processing apparatus 2, gate valve 5 is first opened, and wafer W to be processed is carried in to chamber 10 to be loaded on susceptor 11. Subsequently, DC voltage is applied to electrode plate 20 from DC power supply 22, and then, wafer W is adsorbed on susceptor 11.

Thereafter, the processing gas (for example, a mixed gas including C2F8 gas, O2 gas and Ar gas with a predetermined flow ratio) from shower head 33 is injected in chamber 10 with predetermined flow and flow ratio to set the pressure in chamber 10 at a predetermined value by the main vent line. In addition, the high-frequency power is applied in chamber 10 by susceptor 11 and shower head 33. Accordingly, the processing gas is converted into the plasma in space S, and then, the generated radicals or ions are converged on the surface of wafer W by focus ring 24, such that the surface of wafer W is physically or chemically etched.

In this case, when the plasma abnormal discharge such as a micro-arching occurs, the AE due to the energy emission according to the occurrence of the plasma abnormal discharge is detected by using the ultrasonic sensor. The ultrasonic sensor is one of constituent elements of an abnormality detection system 100 to be described below.

Figure 2:
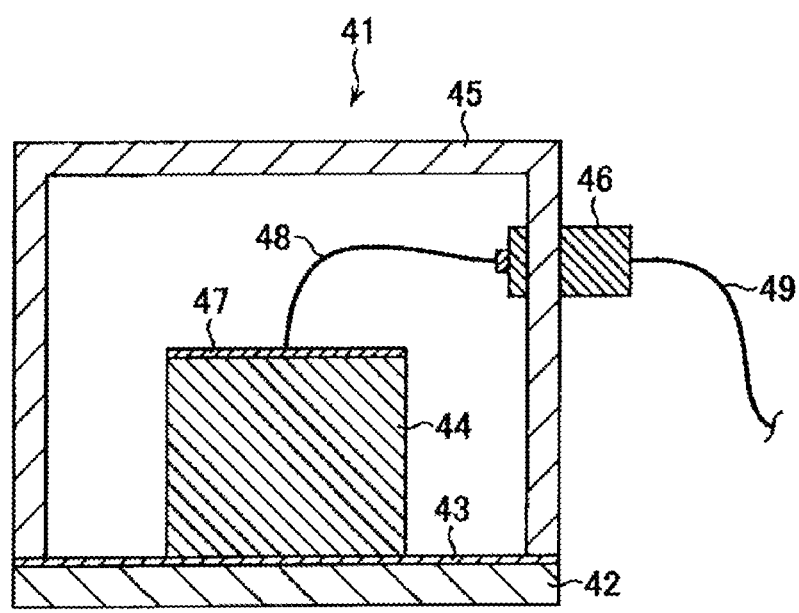
FIG. 2 is a cross-sectional view showing a schematic configuration of an ultrasonic sensor.

FIG. 2 is a cross-sectional view showing a schematic configuration of an ultrasonic sensor. An ultrasonic sensor 41 includes a flat wave-receiving plate 42 including an insulator such as Al2O3, a piezoelectric element 44 (for example, titanate-zirconate-lead-based piezoelectric ceramics) mounted on wave-receiving plate 42 through a metallic film 43 such as a silver deposition film, and a case-type shield case 45 including metal (for example, aluminum or stainless steel) mounted on wave-receiving plate 42 so as to cover piezoelectric element 44.

When piezoelectric element 44 receives a physical vibration such as an ultrasonic wave, voltage having a magnitude corresponding to the magnitude of the vibration is generated. In order to output the voltage signal, a connector 46 exposed inside and outside shield case 45 is disposed at the side wall of shield case 45, such that a metallic film 47 and a connector 46 are connected with each other by an inner wiring 48, and an outer wiring 49 is connected to connector 46, and the voltage signal generated from piezoelectric element 44 is outputted through outer wiring 49.

Ultrasonic sensor 41 is mounted at the outside of a constituent component, for example, chamber 10 or pipe insulator 39 from which the occurrence of the plasma abnormal discharge is expected in plasma processing apparatus 2. In detail, in order to detect the ultrasonic wave propagated to the outer wall of chamber 10 due to the occurrence of the plasma abnormal discharge, wave-receiving plate 42 is closely contacted to the outer wall of chamber 10 to mount ultrasonic sensor 41 on chamber 10.

Meanwhile, depending on constituent components of plasma processing apparatus 2, there is a concern that a leakage current flows into ultrasonic sensor 41 from the constituent component, such that ultrasonic sensor 41 may not exactly detect the abnormal discharge. However, in ultrasonic sensor 41, since wave-receiving plate 42 including the insulator blocks the leakage current, it is possible to avoid the problem. As long as the insulator used in wave-receiving plate 42 can transfer the ultrasonic wave, the insulator is not limited to $Al_2O_3$.

Figure 3:
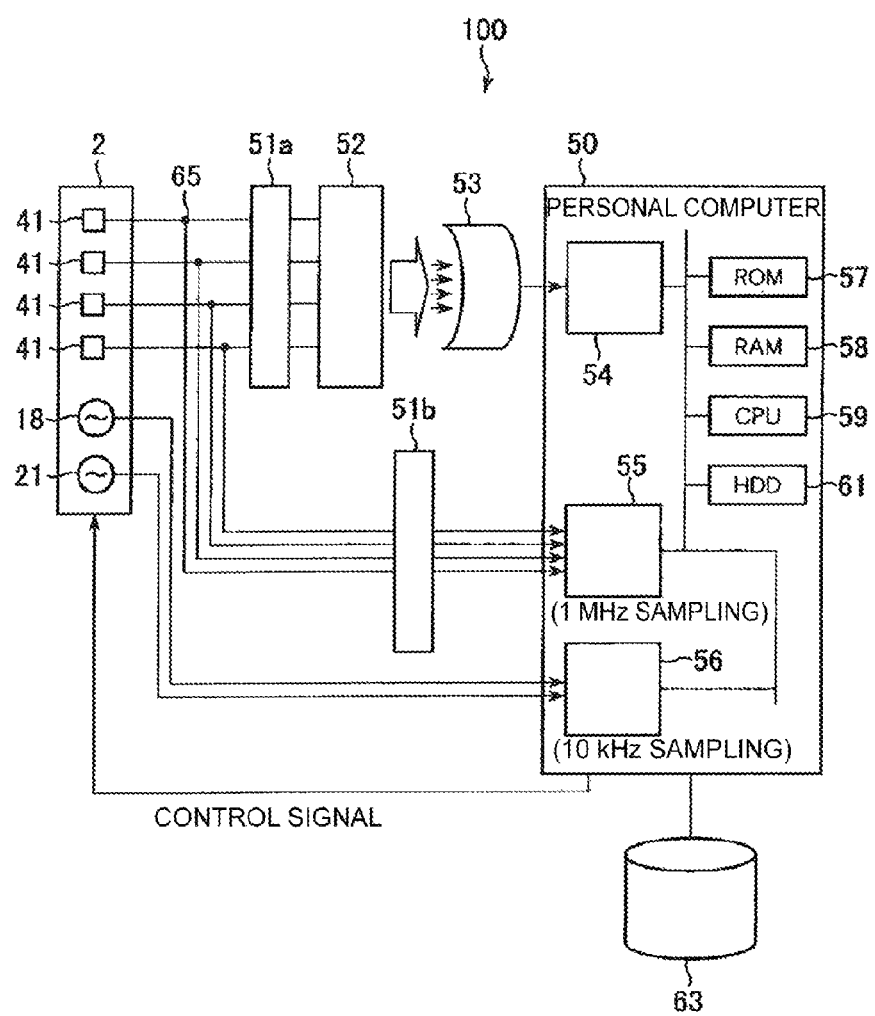
FIG. 3 is a schematic configuration diagram of an abnormality detection system according to an exemplary embodiment of the present invention.

Subsequently, an abnormality detection system of the plasma abnormal discharge occurring in plasma processing apparatus 2 will be described. FIG. 3 is a schematic configuration diagram of an abnormality detection system according to an exemplary embodiment of the present invention.

As described above, since the power outputted from high-frequency power supplies 18 and 21 is monitored in plasma processing apparatus 2, the monitoring signal may be used for the abnormality detection (mainly, the abnormality detection in the plasma generation). However, as described below, when a sampling frequency of the monitoring signal is, for example, 10 kHz, and a sampling frequency of an output signal (hereinafter, referred to as a "sensor signal") of ultrasonic sensor 41 is, for example, 1 MHz, the sensor signal is acquired in detail. Accordingly, the abnormality occurring in plasma processing apparatus 2 is detected and analyzed based on the sensor signal (hereinafter, referred to as "abnormality detection/analysis processing") and the monitoring signal is additionally used for the abnormality detection/analysis.

Abnormality detection system 100 includes an ultrasonic sensor 41 disposed at plasma processing apparatus 2, a distributor 65 distributing sensor signals from ultrasonic sensor 41 to the same signal of a dual system, a filter 51a for removing noise from one sensor signal (the first signal) outputted from distributor 65, a filter 51b for removing noise from the other sensor signal (the second signal) outputted from distributor 65, a trigger 52 generating a trigger signal by detecting a predetermined feature included in the sensor signal passing through filter 51a, an OR circuit 53 performing a predetermined operation (processing) for the trigger signal outputted from trigger 52, and a personal computer (PC) 50 data-processing the output signal from OR circuit 53 and the sensor signal passing through filter 51b.

Abnormality detection system 100 includes a plurality of ultrasonic sensors 41, and as a result, although the abnormality is difficult to be detected by information from one ultrasonic sensor 41, the probability of strongly detecting the abnormality by other ultrasonic sensors 41 may be increased. That is, multivariate (multichannel) analysis analyzing information from the plurality of ultrasonic sensors 41 is performed, such that the high detection precision is implemented. Herein, the number of ultrasonic sensors 41 is four, but is not limited thereto.

In abnormality detection system 100, the sensor signals outputted from ultrasonic sensor 41 are distributed to the same signal of a dual system by distributor 65. As described below, the purpose is to efficiently perform the data-processing of the sensor signal.

The sensor signal outputted from ultrasonic sensor 41 is an analogue voltage signal. The sensor signal includes mechanical vibration and the like generated by an operation of plasma processing apparatus 2 as noise, and in many cases, such noise and the AE having an abnormality such as a plasma abnormal discharge to be detected have different wavelengths. Accordingly, one sensor signal outputted from distributor 65 passes through filter 51a (particularly, a high-pass filter (HPF)) so as to block unnecessary low-frequency noise before inputting the sensor signal to trigger 52. Filter 51a contributes to the judgment of a trigger output condition in trigger 52.

On the contrary, the other sensor signal outputted from distributor 65 passes through filter 51b (particularly, a band-pass filter (BPF)) so as to block unnecessary low-frequency noise before inputting the sensor signal to a data logger board 55 (to be described below) provided in PC 50. In the abnormality detection/analysis processing performed in PC 50, filter 51b contributes to the calculation of a feature quantity of a frequency relationship which is a determination factor of the abnormality.

Trigger 52 is hardware (H/W) determining whether or not ultrasonic sensor 41 detects the abnormality by simply analyzing the sensor signal to extract the predetermined feature included in the sensor signal. Meanwhile, trigger 52 includes software for changing and setting an operation condition of the H/W and condition input means (for example, an operating panel and the like).

Trigger 52 serves as an A/D convertor sampling each sensor signal by, for example, a sampling frequency of 10 kHz. The sampling frequency of trigger 52 may be selected in the range of 10 kHz to 5 MHz.

Trigger 52 serves as a signal generator, and when it is judged that the abnormality did not occur in plasma processing apparatus 2, a signal of '0' representing that judgment is generated, and when a predetermined feature was found, which is suspected that the abnormality occurred is observed, a signal of '1' (hereinafter, referred to as a 'trigger signal') is generated on a regular cycle to be outputted to OR circuit 53. For example, when a peak showing a maximum value larger than a predetermined threshold is detected, trigger 52 judges that the abnormality occurred in plasma processing apparatus 2, such that trigger 52 generates the trigger signal.

An output line of trigger 52 may be installed in every sensor signal or be united into one. Herein, the output line of trigger 52 is installed in every sensor signal. OR circuit 53 includes a four-system input line corresponding to the output line of trigger 52 installed in every four ultrasonic sensors 41.

OR circuit 53 is H/W performing processing by a method for processing first or second trigger signal as described below when OR circuit 53 examines the signal transmitted from trigger 52 to receive the trigger signal.

The method for processing the first trigger signal by OR circuit 53 is a method that transmits all the trigger signals to PC 50 without a substantial delay according to a time series regardless of which input line the trigger signal is received from, when the trigger signal is received from trigger 52. Similar to the case where the layout number of ultrasonic sensors 41 is small (for example, two), although a lot of trigger signals are generated, the first method may be used for the case where increase in the load of the abnormality detection/analysis processing in PC 50 is limited.

The method for processing the second trigger signal by OR circuit 53 is a method that integrates the trigger signals generated for a predetermined period into one trigger signal to output the integrated trigger signal to PC 50 regardless of which one among four-system input lines the trigger signal is received from.

Specifically, when OR circuit 53 receives a first trigger signal from trigger 52, it regards that all the trigger signals received within a predetermined period from the receiving time (hereinafter, referred to as an "integrated period") results from the same abnormality as the abnormality that is a cause of the first trigger signal, and then, generates a trigger signal (hereinafter, referred to as a "representative trigger signal") which integrates the trigger signals into one signal, thereby outputting the representative trigger signal to PC 50. After the representative trigger signal is outputted to PC 50, the first received trigger signal is a start reference of the next integrated period.

Even in the method for processing the first or second trigger signal, since one line is enough for the output line from OR circuit 53 to PC 50, OR circuit 53 includes one output line. Meanwhile, trigger 52 and OR circuit 53 may be configured as one H/W.

PC 50 performs the abnormality detection/analysis processing for specifying the abnormality occurring in plasma processing apparatus 2, based on the trigger signal outputted from OR circuit 53 or the representative trigger signal and the sensor signal passing through filter 51b.

Hereinafter, it is assumed that OR circuit 53 outputs the representative trigger signal according to the method for processing the second trigger signal as described above in abnormality detection system 100, and a configuration of PC 50 and a data processing method will be described.

PC 50 includes a CPU 59, a RAM 58 for temporally storing program data or data to be an operation target in order to process the abnormality detection/analysis, a ROM 57 for storing a booting program or a program for an operating system (OS), and a hard disk drive (HDD) 61 as a storage device for storing a program used in the abnormality detection/analysis processing, intermediate data acquired during the abnormality analysis, the analyzed result, or the like.

PC 50 further includes, for example, an input means such as a keyboard or a mouse, a liquid crystal display (LCD) as a monitor, a graphic board, a drive handling a storing medium such as a CD-ROM or a DVD-RAM, an interface for connection to a communication link such as a LAN or the Internet.

Further, PC 50 includes a trigger generation time counter 54 specifying a generation time of the representative trigger signal (hereinafter, referred to as a "trigger generation time") by receiving the representative trigger signal outputted from OR circuit 53, a data logger board 55 for digital-sampling the four-system sensor signals passing through filter 51b every sensor signal with a predetermined frequency to store the sampled sensor signals as the digital data, and a data logger board 56 for digital-sampling monitor signals of high-frequency power supplies 18 and 21 by a predetermined frequency to store the sampled monitor signals as digital data.

Trigger generation time counter 54 and data logger boards 55 and 56 are mounted on, for example, a PCI bus of PC 50 to be controlled by a driver installed in PC 50.

Trigger generation time counter 54 includes an inner clock, and for example, a time receiving the representative trigger signal is recognized as the trigger generation time. As described above, the representative trigger signal is generated at the time when the integrated period elapses from the generation time of the first trigger signal in trigger 52 generating the representative trigger signal as a reference. As a result, a time lag occurs between an actual occurrence time of the abnormality in plasma processing apparatus 2 and the trigger generation time. Accordingly, as described below, PC 50 performs the abnormality detection/analysis processing by considering the time lag.

Data logger board 55 serves as an A/D converter and high-speedily samples the sensor signal passing through filter 51b by, for example, a frequency of 1 MHz to convert the sensor signal into digital data (hereinafter, referred to as "high-speed sampling data"), and then, stores the digital data.

By using the sampling frequency of 1 MHz, the abnormal discharge such as a micro-arching which ends at several micro-seconds after occurring can also be detected. Meanwhile, the sampling frequency of data logger board 55 may be selected in the range of 500 kHz to 5 MHz.

Data logger board 55 also includes an inner clock, and the high-speed sampling data as time-series data according to the inner clock is stored in data logger board 55 and moves to HDD 61 on a predetermined cycle to be stored. Accordingly, it is possible to prevent overflow of the accumulated data in data logger board 55.

The inner clock of data logger board 55 and the inner clock of trigger generation time counter 54 are synchronized. The high-speed sampling data shows the features caused by the abnormality in the occurrence time of the actual abnormality in plasma processing apparatus 2, but the time lag occurs between the occurrence time of the actual abnormality in plasma processing apparatus 2 and the trigger generation time as described above. As described below, the high-speed sampling data is handled in PC 50 in consideration of the time lag.

The monitor signal is converted into digital data (hereinafter, referred to as "low-speed sampling data") by using the sampling frequency of, for example, 10 kHz in data logger board 56.

Data logger board 56 also includes an inner clock synchronized with the inner clock of trigger generation time counter 54, and the low-speed sampling data as time-series data according to the inner clock is stored in data logger board 56 and moves to HDD 61 on a predetermined cycle to be stored. Accordingly, it is possible to prevent overflow of the accumulated data in data logger board 56.

As described above, abnormality detection system 100 acquires all the detailed data for specifying the abnormality occurring in plasma processing apparatus 2 as the high-speed sampling data. However, since the data quantity of the high-speed sampling data is huge, when all the high-speed sampling data is analyzed, a lot of processing costs and time are required. Considering the time lag between the occurrence time of the actual abnormality in plasma processing apparatus 2 and the trigger generation time, the features on the abnormality shown in the high-speed sampling data need to be exactly extracted.

Accordingly, schematically, when trigger generation time counter 54 determines the trigger generation time by receiving the representative trigger signal, PC 50 cuts the data of a predetermined period (time width) before and after the trigger generation time among the high-speed sampling data stored in HDD 61 every four-system sensor signal (hereinafter, the cut data is referred to as "limited data") to analyze the cut data. As a result, it is judged whether or not the abnormality actually occurred and particularly, which abnormality occurred when the abnormality occurred. PC 50 executes the abnormality detection/analysis program for performing a series of processing.

As described above, by using the limited data in the abnormality detection/analysis processing, data throughput is reduced to lower the processing costs, and the abnormality detection of high precision may be efficiently performed to enable the abnormality detection/analysis processing in real time. Further, since the determination of the trigger generation time, the collection of the high-speed sampling data, and the abnormality detection/analysis processing are separately performed by different threads, the delay of each processing can be prevented. The method of the abnormality detection/analysis processing in PC 50 will be described below in detail.

When it is judged that the abnormality interrupting the operation of plasma processing apparatus 2 occurred through the analysis of the high-speed sampling data, abnormality detection system 100 may notify the alarm to plasma processing apparatus 2, or transmit control signals for delaying or performing the processing start of the next wafer W to plasma processing apparatus 2.

A knowledge database (DB) 63, which stores various data used in the abnormality detection/analysis processing or the abnormality detection/analysis processing result, and furthermore, relevant information of the abnormality detection/analysis processing result, is connected to PC 50.

Among the high-speed sampling data stored in HDD 61, since data other than the limited data is basically unnecessary, the data is removed from HDD 61 after the limited data is confirmed and then, the limited data is appropriately transferred from HDD 61 to knowledge DB 63 to be stored.

The abnormality detection/analysis processing result or the process condition (recipe data) used in the processing of wafer W is linked to the limited data to be stored in knowledge DB 63. Kinds, causes, countermeasures and the like occurring in plasma processing apparatus 2 are linked to the abnormality detection/analysis processing result to be stored in knowledge DB 63.

Various data stored in knowledge DB 63 are helpful in setting various parameters (for example, definition of a normal model or a model for authorization of the abnormal pattern, definition of various thresholds and the like as described below) used in the subsequent abnormality detection/analysis processing.

Meanwhile, an abnormality detection system which is accompanied with a plasma processing apparatus having the same constitution as plasma processing apparatus 2 and disposed at another place may be accessed to access knowledge DB 63 by using a communication link. Accordingly, information on the abnormality occurring in the plasma processing apparatus disposed at another place is accumulated in knowledge DB 63 to be helpful to the abnormality detection/analysis processing of plasma processing apparatus 2. Further, the abnormality detection system which is accompanied with the plasma processing apparatus disposed at another place draws out the required information from knowledge DB 63, such that it is possible to easily cope with the abnormality occurring in the plasma processing apparatus.

Subsequently, a method of abnormality detection/analysis processing by abnormality detection system 100 will be described. First, the method of abnormality detection/analysis processing will be schematically described, and thereafter, main processing of the abnormality detection/analysis processing will be described in detail.

Figure 4:
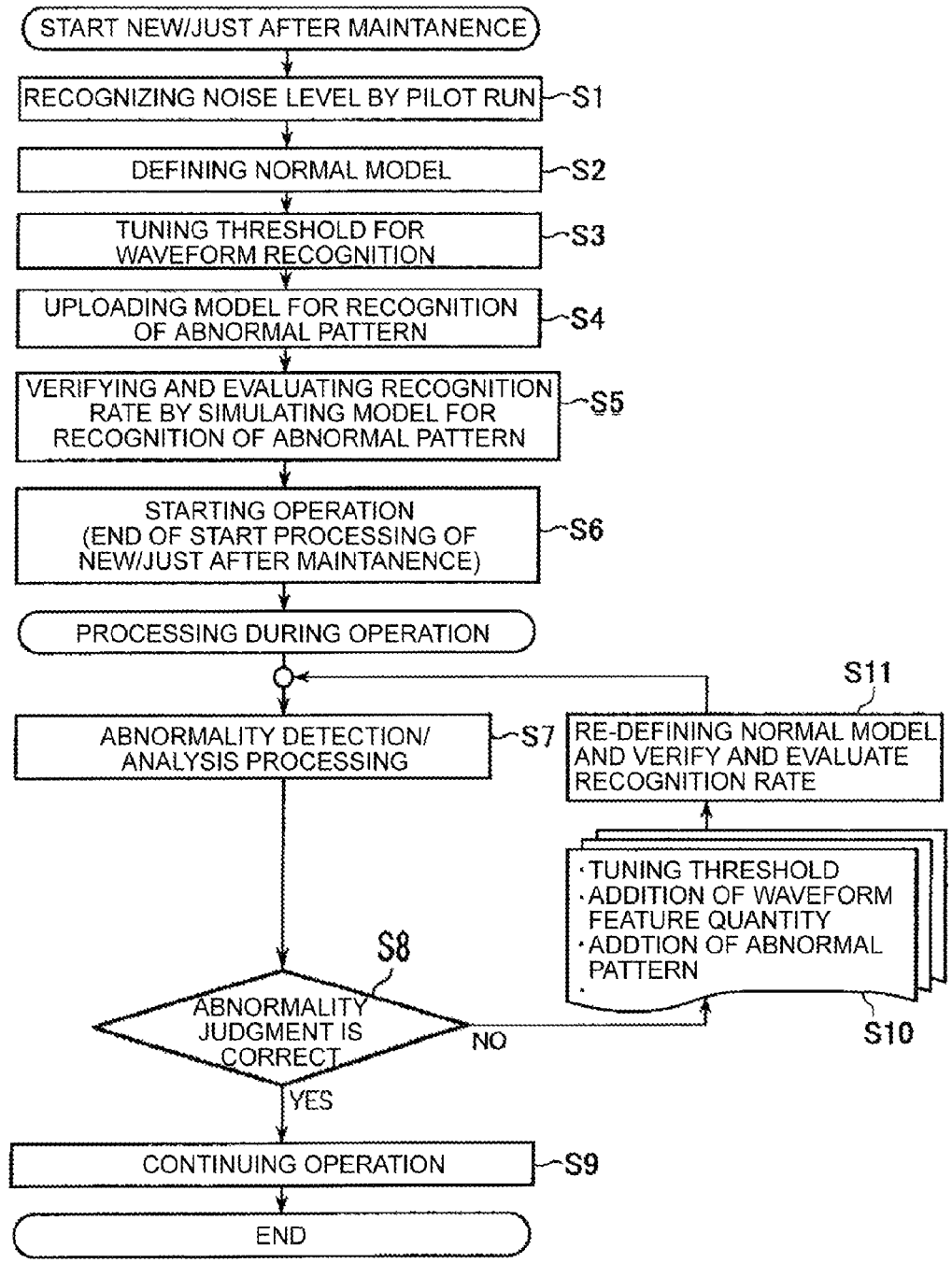
FIG. 4 is a flowchart showing an outline of an operation embodiment of an abnormality detection system.

FIG. 4 is a flowchart showing an outline of an operation form of abnormality detection system 100.

Abnormality detection system 100 starts simultaneously with a new start or a start just after maintenance of plasma processing apparatus 2. In this case, since in some cases, the apparatus condition of plasma processing apparatus 2 is unclear or changed, first of all, the noise level recognition of ultrasonic sensor 41 and monitor sensors of high-frequency power supplies 18 and 21 is performed by a pilot run (mass-production trial) (step S1).

When comparing the noise level measured at step S1 with a normal model, if the noise level is in a permissible range, the normal model is defined by tuning a S/N ratio of the normal model based on the measured result of the pilot run (step S2). Meanwhile, the normal model is a waveform defined by statistics after performing predetermined filter processing to time-series data from each ultrasonic sensor 41 in a defined period such as an idle state, plasma generation and the like (for example, wafer transferring) of plasma processing apparatus 2, for example, parameters such as maximum, minimum, average, distribution and the like.

Meanwhile, although not shown in FIG. 4, when the noise level measured at step S1 represents the abnormality of any apparatus or has a large difference from the known normal model, the alarm is notified, and then, plasma processing apparatus 2 is locked and becomes a checking subject of an operator or a manager.

After the normal model is defined at step S2, a threshold for waveform recognition is tuned (step S3). For example, a threshold for generating the trigger signal or a threshold for peak judgment or feature quantity extraction in the waveform shown in down sampling data as be described below is determined in trigger 52.

Subsequently, a model for the abnormal pattern recognition stored in HDD 61 (or knowledge DB 63) is uploaded (step S4). The model for the abnormal pattern recognition is various feature quantities representing the waveform and is used in the pattern recognition of the waveform based on the limited data (high-speed sampling data) in PC 50 to be stored in, for example, RAM 58.

Meanwhile, at step S4, one or a plurality of models for abnormal pattern recognition may be uploaded every abnormality with a known cause, and a model for abnormal pattern recognition representing a waveform with an unclear cause as the detected abnormality in the past may also be uploaded.

Subsequently, a recognition rate due to a simulation of the model for abnormal pattern recognition is verified and evaluated (step S5). Step S5 may be performed by using the high-speed sampling data and the low-speed sampling data acquired in the pilot run, and may also be performed by performing a new pilot run. At step S5, when a constant recognition rate (for example, 90%) is acquired, the processing for the new start and the start just after the maintenance ends, such that plasma processing apparatus 2 and abnormality detection system 100 can be generally operated (step S6).

Meanwhile, although not shown in FIG. 4, when the constant recognition rate is not acquired at step S5, steps S2 to S4 are repeated until the constant recognition rate is acquired.

Subsequently, when plasma processing apparatus 2 is driven, under the condition that has been set up until step S5, plasma processing apparatus 2 is monitored by abnormality detection system 100 (processing start during an operation). If the abnormality is detected during the driving of plasma processing apparatus 2 (trigger 52 generates the trigger signal), abnormality detection system 100 performs the abnormality detection/analysis processing for specifying the abnormality (step S7).

From the result acquired in the abnormality detection/analysis processing of step S7, it is judged whether the abnormality is exactly judged (step S8). For example, when the recognition rate of the pattern recognition with the model for abnormal pattern recognition is low, it is judged that the judgment of abnormality is incorrect ("NO" at step S8), such that various kinds of parameters are reset (step S10).

At step S10, for example, tuning of the threshold, addition of the waveform feature quantity, addition of the model for abnormal pattern recognition and the like are performed and thereafter, re-definition of the normal model and verification and evaluation of the recognition rate are performed (step S11). At step S11, when the constant recognition rate is acquired, the process returns to step S7 (abnormality detection/analysis processing).

Meanwhile, although not shown in FIG. 4, when the constant recognition rate is not acquired at step S11, steps S10 to S11 are repeated until the constant recognition rate is acquired.

At step S8, when it is judged that the judgment of abnormality is correct ("YES" at step S8), abnormality detection system 100 is continuously operated (step S9) and then, plasma processing apparatus 2 is monitored until plasma processing apparatus 2 stops (processing ends during an operation).

Subsequently, a detailed order of step S7 (abnormality detection/analysis processing) will be described.

Figure 5:
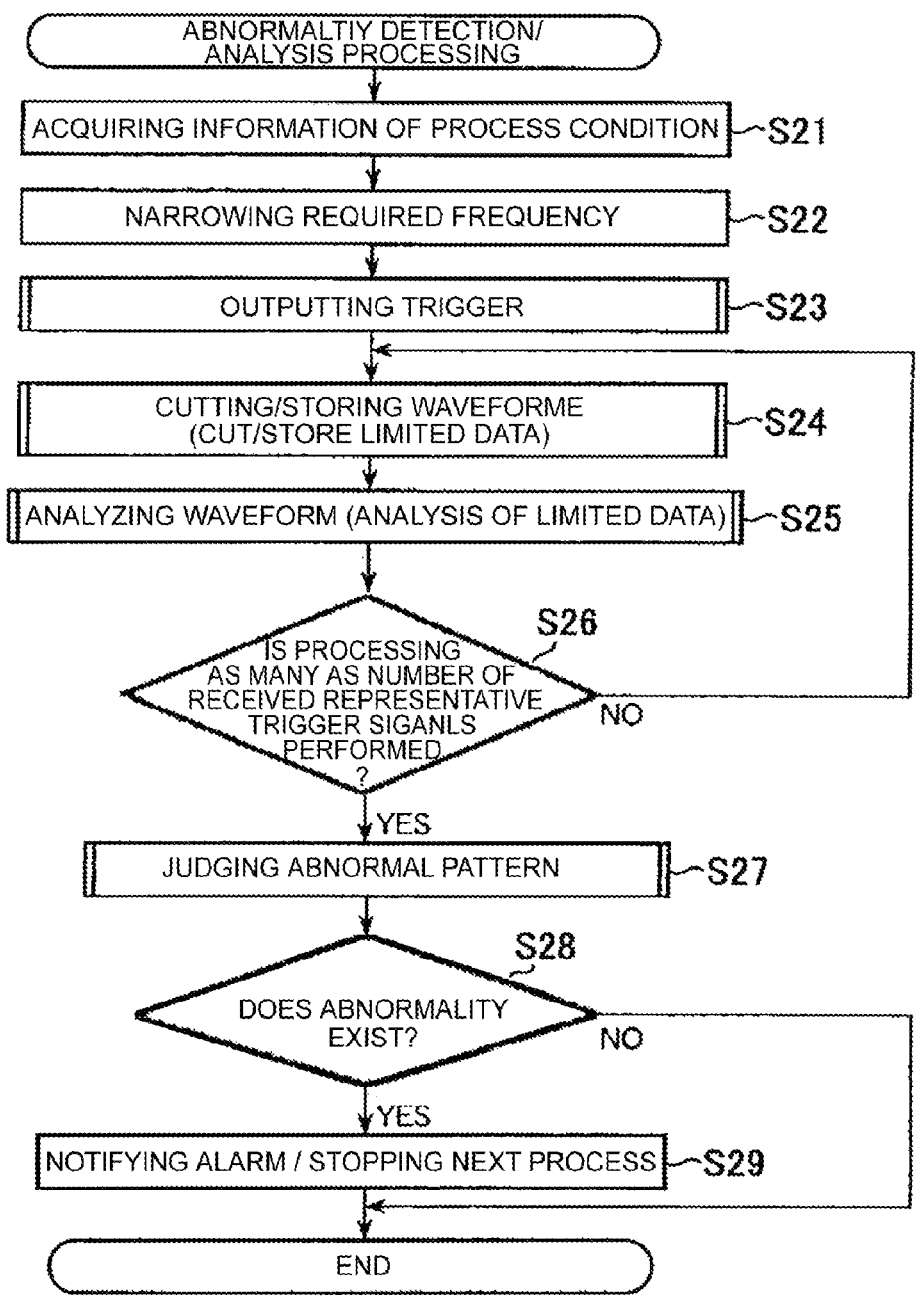
FIG. 5 is a flowchart showing a schematic order of a method of processing abnormality detection/analysis by an abnormality detection system.

FIG. 5 is a flowchart showing a schematic order of a method of abnormality detection/analysis processing.

First, information on a process condition (recipe data) of wafer W is acquired (step S21). For example, when only the abnormality occurring during the plasma generation is desired to be detected, the high-speed sampling data and the low-speed sampling data may be acquired by acquiring the process condition for only a period from the generation start of the plasma to the end thereof.

When the sensor signal starts to be received from ultrasonic sensor 41, the sensor signals are distributed as the same two-system signal by distributor 65, and then, one signal is inputted to trigger 52 after a frequency band is narrowed by filter 51*a* and the other signal is inputted to PC 50 (data logger board 55) after the frequency band is narrowed by filter 51*b* (step S22).

When it is detected that a peak having a maximum value larger than a predetermined threshold exists in the received sensor signal, trigger 52 generates the trigger signal to output the generated trigger signal to OR circuit 53. When the trigger signal is received, OR circuit 53 generates the representative trigger signal according to the method for processing the second trigger signal described above to output the representative trigger signal to PC 50 (step S23).

After step S22, the sensor signal directly inputted to PC 50 is converted into the high-speed sampling data by data logger board 55, temporally stored, and transferred to and stored in HDD 61 on a regular cycle. When trigger generation time counter 54 receives the representative trigger signal from OR circuit 53, the trigger generation time is determined and then, the limited data is cut from the high-speed sampling data (step S24), and unnecessary data other than the limited data is removed.

Considering that the AE due to the abnormality occurring in plasma processing apparatus 2 decreases for a predetermined period after the occurrence, and rapidly generates the trigger signal after the occurrence, a period of the limited data cut at step S24 may be set shortly by considering the integrated period at a period before the trigger generation time and set long so that the peak waveform is not disconnected in midstream at a period after the trigger generation time.

Subsequently, a waveform analysis of the limited data is performed (step S25). Details of the waveform analysis method will be described below. Since the processing of step S25 needs to be performed for the cut limited data with respect to all the representative trigger signals generated in OR circuit 53, it is judged whether the processing as many as the number of the received representative trigger signals is performed (step S26).

When the processing as many as the number of the received representative trigger signals ends ("YES" at step S26), the judgment of the abnormal pattern is performed (step S27). In this case, although the abnormality is difficult to be specified only from the sensor signal of one ultrasonic sensor 41, by comparing the sensor signals acquired from four ultrasonic sensors 41, probability capable of specifying the abnormality cause may be largely increased.

Meanwhile, until the processing as many as the number of the received representative trigger signals ends ("NO" at step S26), the processing of steps S24 and S25 is repeated.

Based on the judgment result of step S27, it is judged whether the abnormality actually occurred (step S28). When it is verified that the abnormality occurred ("YES" at step S28), PC 50 transmits the signals for perform the alarm notification or stop of the next process to plasma processing apparatus 2 (step S29) and ends the abnormality detection/analysis processing.

Meanwhile, when it is not verified that the abnormality occurred and it is judged that the abnormality occurred, but measures such as the alarm notification or the stop of the next process does not need to be taken ("NO" at step S28), the abnormality detection/analysis processing ends. Meanwhile, when the abnormality detection/analysis processing ends, various data acquired at steps S24, S25 and S27 are stored in knowledge DB 63.

Steps S23, S24, S25 and S27 described above will be described below in detail.

Figure 6:
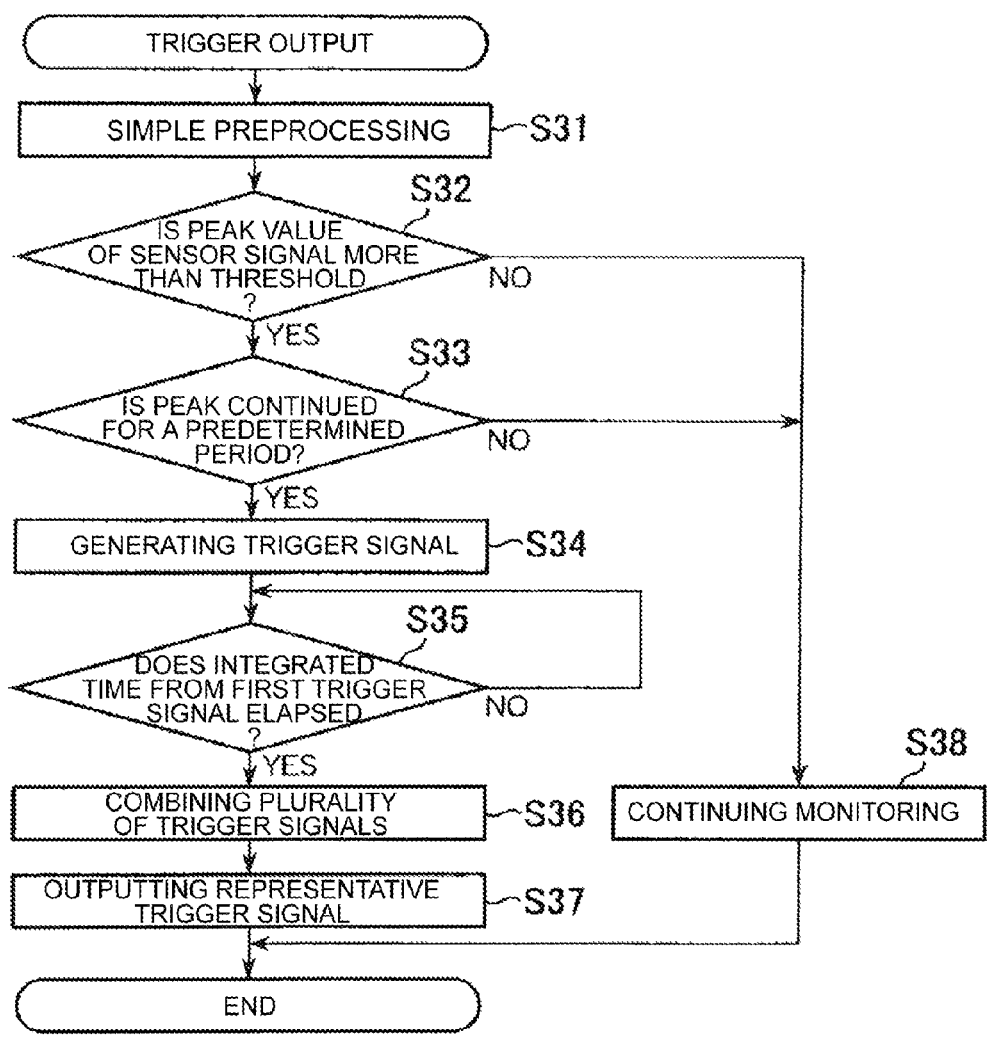
FIG. 6 is a flowchart showing a detailed order of step S23 (trigger output) of FIG. 5.

FIG. 6 is a flowchart showing a detailed order of step S23 (trigger output) of FIG. 5.

The sensor signal passing through filter 51a is inputted to trigger 52 and then, simple preprocessing (herein, digital-sampling processing at 10 kHz) is performed (step S31).

Based on the sampling data acquired at step S31, it is judged whether or not a peak having a maximum value larger than the threshold exists in the sensor signal (step S32). When the peak having a maximum value larger than the threshold exists ("YES" at step S32), in order to distinguish the peak from a peak of noise or the like, it is judged whether the peak is continued for a predetermined period or more, that is, a time width of the predetermined period or more exists in the peak (step S33).

When the peak is continued for a predetermined period or more ("YES" at step S33), trigger 52 generates the trigger signal to output the generated trigger signal to OR circuit 53 (step S34). OR circuit 53 judges whether the integrated period from the first trigger signal elapsed (step S35), and then, waits for the elapse of the integrated period ("NO" at step S35).

If the integrated period elapses at step S35 ("YES" at step S35), OR circuit 53 couples the trigger signals received within the integrated period to generate the representative trigger signal (step S36), and then, outputs the representative trigger signal to PC 50 (step S37).

At step S37, the first trigger signal received after outputting the representative trigger signal is a reference trigger signal of generating the next representative trigger signal. When the judgment of steps S32 and S33 is "NO", the monitoring is continuously performed (step S38) and the processing of step S23 ends by the end of steps S37 and S38.

Figure 7:
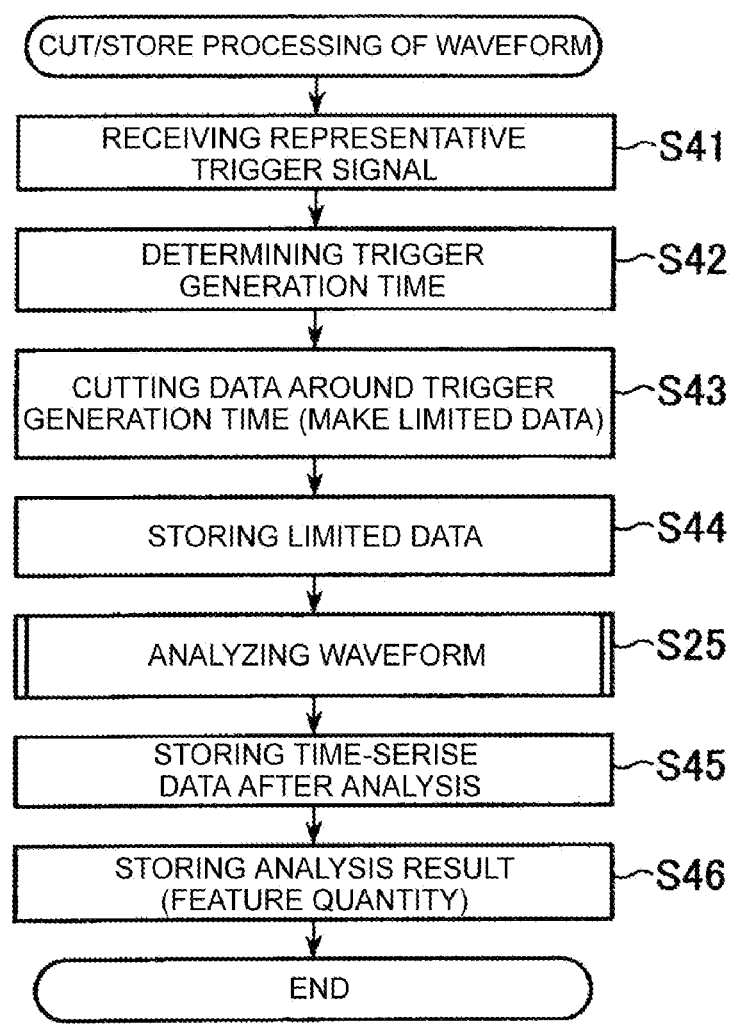
FIG. 7 is a flowchart showing a detailed order of step S24 (waveform cut/store) of FIG. 5.

FIG. 7 is a flowchart showing a detailed order of step S24 (waveform cut/store).

When the representative trigger signal is received (step S41), trigger generation time counter 54 installed on PC 50 determines the trigger generation time (step S42). When the trigger generation time is determined at step S42, cutting of trigger generation time peripheral data (making of the limited data) for the high-speed sampling data and the low-speed sampling data is performed by applying a predetermined period to the trigger generation time (step S43). Meanwhile, the "predetermined period" is determined in consideration of the integrated period required for the generation of the representative trigger signal.

The limited data cut at step S43 is stored in HDD 61 (step S44), and unnecessary data of the high-speed sampling data and the low-speed sampling data is removed from HDD 61.

Subsequently, the analysis of the limited data (waveform analysis of S25) is performed and the time-series data acquired at step S25 is stored in HDD 61 (step S45) to be appropriately transferred to and stored in knowledge DB 63. Further, the analysis result acquired at step S25 (the feature quantity of the peak representing the abnormality) is stored in HDD 61 (step S46), and the waveform cut/store processing ends.

Figure 8:
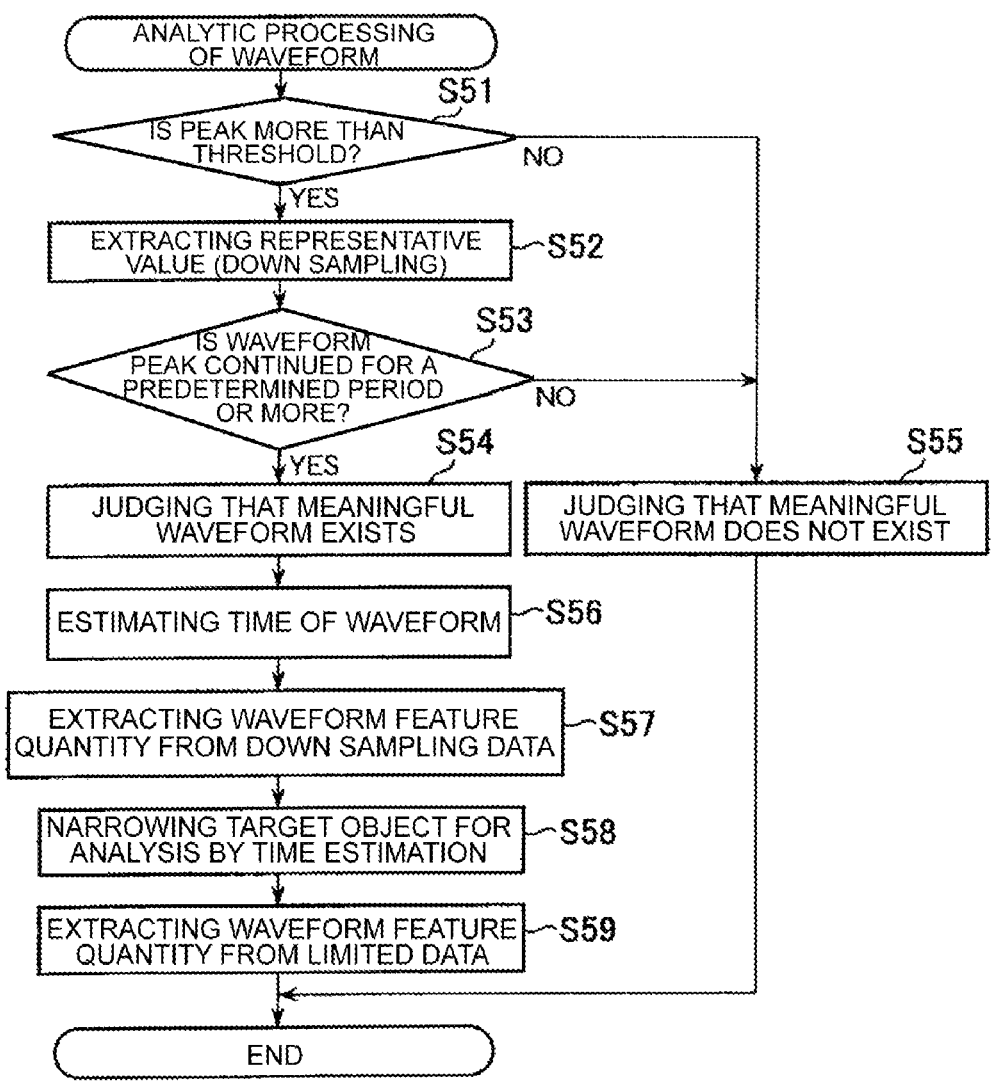
FIG. 8 is a flowchart showing a detailed order of step S25 (waveform analysis) of FIG. 5.

FIG. 8 is a flowchart showing a detailed order of step S25 (waveform analysis).

Four limited data for one representative trigger signal exist. As a result, it is judged whether a peak value (maximum amplitude) is larger than a predetermined threshold every limited data (whether or not a peak having a peak value larger than the threshold exists) (step S51). When the peak value is less than the threshold ("NO" at step S51), it is judged that a meaningful waveform does not exist (step S55), and the waveform analysis processing for the limited data ends.

When the peak value is larger than the threshold ("YES" at step S51), a representative value extraction (down sampling) is performed (step S52). The sensor signal generated by ultrasonic sensor 41 represents a vibrating waveform changed between a plus value and a minus value of a voltage value, such that the maximum amplitude (absolute value) may be adopted as the representative value. In this case, at step S52, the minus value is converted into the plus value to overlap with the original plus value, and waveform data connecting the maximum amplitude values of the waveform thus obtained is processed as down sampling data having a sampling frequency of, for example, 10 kHz.

Meanwhile, minimum amplitude, average amplitude, and the like in addition to the maximum amplitude may be as the representative value that can be adopted at step S52 and may be selected according to a characteristic of a signal to be detected. By reducing the number of data at step S52, a data processing load at the next steps S53 to S58 may be reduced and a data processing time may be shortened.

Subsequently, based on the waveform of the acquired down sampling data, it is judged whether the peak is continued for a predetermined period or more (step S53). For example, it is judged whether a height of the waveform is maintained over the time width of the predetermined period or more by a height of 15% or more of the maximum amplitude.

When the peak is not continued for the predetermined period or more ("NO" at step S53), it is judged that a meaningful waveform does not exist (step S55), and the waveform analysis processing for the down sampling data and the limited data as the cause thereof ends.

When the peak is continued for the predetermined period or more ("YES" at step S53), it is judged that a meaningful waveform exists (step S54) and the time of the waveform (time for specifying the waveform) is estimated (step S56). As the time estimation method, in a order in which the data processing time is short, energy monitoring, cross-correlation value monitoring, a local normal AR model and the like may be used. In the case of using the energy monitoring method, the time representing the maximum amplitude may be the time of the waveform.

Thereafter, the waveform feature quantity is extracted from the down sampling data (step S57). The waveform feature quantity may include maximum energy (temporal integral value of the maximum amplitude), a time representing the maximum energy, a reaching time of the maximum energy (a first time, for example, below 25% of the maximum energy by counting forward the time representing the maximum energy), an extinction time of the maximum energy (a first time, for example, below 25% of the maximum energy by counting backward the time representing the maximum energy), intermittent wave/continuous wave (the continuous wave is, for example, not below 25% of the maximum energy for the predetermined period and the intermittent wave is for example, below 25% of the maximum energy) and the like.

From the estimation time of the waveform acquired at step S56 and the waveform feature quantity acquired at step S57, the analysis subject (range) is narrowed (step S58). With respect to the analysis subject narrowed at step S58, the waveform feature quantity is extracted from the limited data (step S59). In detail, the waveform feature of the limited data (sampling frequency: 1 MHz) is extracted by a fast Fourier transform (FFT).

The waveform feature quantity may include a FFT start time (=the reaching time of the maximum energy), a FFT end time (a first time at which the number of FFT samples becomes the power of 2 by progressing forward the extinction time of the maximum energy), the number of FFT samples (the number of samples used in the FFT and for example, 16348 may be the upper limit), a maximum peak frequency (a frequency representing the maximum amplitude), an average frequency (a frequency in which a peak area (energy) is beyond 50% of the entire peak area), a ratio of a reference frequency or more (a ratio of the reference frequency (for example, 20% of the sampling frequency) or more) and the like. As described above, the waveform analysis processing ends.

Figure 9:
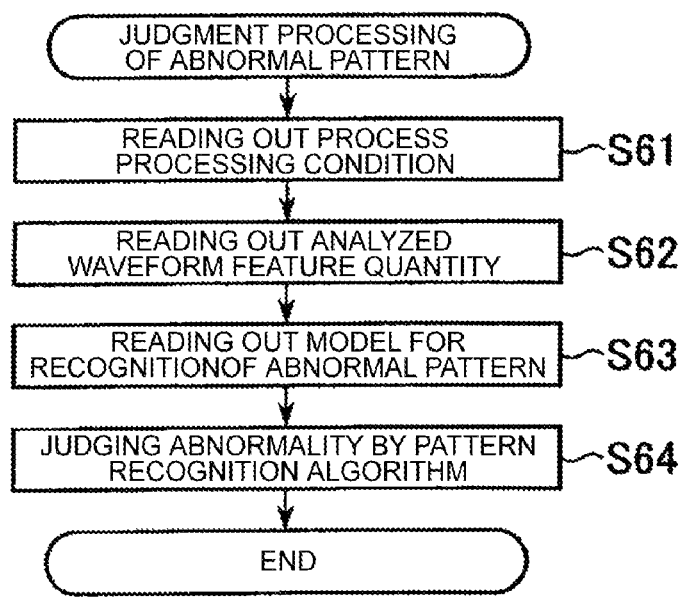
FIG. 9 is a flowchart showing a detailed order of step S27 (judgment of abnormal pattern) of FIG. 5.

FIG. 9 is a flowchart showing a detailed order of step S27 (judgment of abnormal pattern).

First, the process processing condition is read (step S61). Since abnormality to occur may be limited based on the read process processing condition, the model for abnormal pattern recognition may be compressed to shorten a judgment time. Further, when the occurring abnormality is judged, accuracy may increase.

Subsequently, the waveform feature quantity acquired in the waveform analysis (step S25) is read (step S62), and the model for abnormal pattern recognition is also read (S63). Further, it is judged which abnormality occurred by a pattern recognition algorithm of comparing the waveform feature quantity read at step S62 and the model for abnormal pattern recognition read at step S63 (step S64). As the pattern recognition algorithm, a known method may be used by expanding, for example, a support vector machine (SVM) by multistage judgment. Thus, the judgment processing of abnormal pattern ends.

Subsequently, a modified example of abnormality detection system 100 will be described.

Modified Example 1

The configurations of trigger generation time counter 54 and data logger boards 55 and 56 are not limited to the above exemplary embodiments, and the clock control of trigger generation time counter 54 and data logger boards 55 and 56 may be performed by one external reference synchronized clock.

Modified Example 2

In the exemplary embodiment, the plurality of trigger signals are integrated to one representative trigger signal in OR circuit 53 (the method for processing the second trigger signal), but as a method for generating the representative trigger signal, a method to be described below may also be used.

That is, a buffer port and a time counter instead of trigger generation time counter 54 are installed in PC 50, such that the external reference synchronized clock gives the time information to the time counter. According to the above method for processing the first trigger signal, OR circuit 53 successively outputs the trigger signals received from trigger 52 to the buffer port according to the time series. A counter value outputted from the time counter is inputted to the buffer port. Accordingly, the counter value is given to the trigger signal.

The buffer port integrates the plurality of trigger signals within a predetermined period to one representative trigger signal. In this case, since each trigger signal includes the time information, for example, the time information of the first trigger signal within the predetermined period may be used as the trigger generation time of the representative trigger signal.

Accordingly, in the case of using the above method for processing the second trigger signal, the trigger generation time of the representative trigger signal is the time at which the integrated period from the generation time of the first trigger signal generating the representative trigger signal elapses, but in the method, the trigger generation time of the representative trigger signal may be set as a time close to the time when the abnormality actually occurs in plasma processing apparatus 2.

Modified Example 3

As another generation method of the representative trigger signal in OR circuit 53, the first received trigger signal as the representative trigger signal is outputted to PC 50 and then, until the time corresponding to the integrated period elapses, a method in which the received trigger signal is not outputted to PC 50 may be used. Even in the method, the trigger generation time determined by trigger generation time counter 54 may be set as a time close to the time when the abnormality actually occurs in plasma processing apparatus 2.

Modified Example 4

In the exemplary embodiment, the cutting of the limited data is performed from the high-speed sampling data stored in HDD 61, but is not limited thereto, and when the high-speed sampling data is stored in data logger board 55, the limited data may be cut according to the reception of the representative trigger signal, and while the cut limited data is transferred to and stored in the HDD 61 from data logger board 55, the data other than the limited data may be removed from data logger board 55. The same method may also be used for the low-speed sampling data.

Further, when the limited data is specified from the high-speed sampling data and the unnecessary data is removed, it is verified that a peak of a predetermined threshold or more does not exist in the unnecessary data and then, the removal may be performed. Although the limited data is specified, the unnecessary data may not be removed for a predetermined time, the high-speed sampling data may be periodically transferred to the HDD 61 to be stored for a predetermined period, and the unnecessary data may be appropriately removed.

Modified Example 5

In the exemplary embodiment, at step S51 of the waveform analysis processing, the limited data in which it is determined that the peak value is less than the predetermined threshold is excluded from the subsequent analysis subject and at step S53, the down sampling data in which the peak is not continued for the predetermined period or more and the limited data as the cause are excluded from the subsequent analysis subject. However, when four limited data corresponding to one representative trigger signal is determined as one group and the limited data in which it is judged that the peak value is more than the predetermined threshold exists in the group, or even though one down sampling data in which the peak is continued for the predetermined period or more exists in the group, the processing method may be configured so that the next processing is performed to all the data of the group. According to this, the interrelationship between the sensor signals from four ultrasonic sensors 41 may be comprehended.

Modified Example 6

Probability, in which the abnormal discharge occurring during the plasma generation in plasma processing apparatus 2 is shown in the monitor signal, is also high.

Accordingly, the trigger signal may be generated based on the monitor signal. Further, the same processing as the processing for the sensor signal may be performed for the monitor signal and the cause of the abnormality may be judged and determined from the feature quantities of the waveforms represented by the sensor signal and the monitor signal.

Modified Example 7

When the sensor signal is sampled at a high speed of 1 MHz, actually, thinning data which is the same as the sampling at 10 kHz is created together with the high-speed sampling data, such that the data processing up to the process of narrowing the analysis subject by the time estimation (step S58) may be performed by using the thinning data.

However, the method may be limited to the case where it is empirically verified that although the determination of the peak value of step S51 of using the sampling data at 1 MHz is performed by the sampling data at 10 kHz, there is no problem.

As described above, the exemplary embodiments of the present invention are described, but the present invention is not limited to the exemplary embodiments. The present invention can also be achieved by supplying a storage medium storing a program of software implementing the functions of each of the above-described exemplary embodiments to PC 50 or an external server and by reading and executing the program code stored in the storage medium by a CPU of PC 50 or the external server.

In this case, the program code read from the storage medium implements the functions of each of the above-described exemplary embodiments, and the storage medium storing the program code configures the present invention.

As the storage medium for supplying the program code, for example, a floppy (registered trademark) disk, a hard disk, a magneto-optical disk, an optical disk such as a CD-ROM, a CD-R, a CD-RW, DVD-ROM, DVD-RAM, DVD-RW and DVD+RW, a magnetic tape, a non-volatile memory card, other ROMs, etc., may be used. The program code may be downloaded through a network. In this case, the program code is downloaded from other computers or databases (not shown) connected to the Internet, commercial networks, or local area networks to be supplied.

The functions of each of the above-described exemplary embodiments may be implemented by executing the program code read by the CPU, and an operating system (OS) operated on the CPU performs some or all of the actual processing based on the instruction of the program code, and the functions of each of the above-mentioned exemplary embodiments may also be implemented according to the processing.

The program code read from the storage medium is recorded in a memory included in a function extension board inserted into PC 50 or the external server or a function extension unit connected to PC 50 or the external server, and then, the CPU installed in the function extension board or the function extension unit executes some or all of the actual processing based on the instruction of the program code and the functions of each of the above-described exemplary embodiments by the processing may also be implemented.

A type of the program code may be an object code, a program code executed by an interpreter, script data supplied to the OS and the like.

In the plasma processing apparatus according to the exemplary embodiments, in order to detect the plasma abnormal discharge, the sensor signal from the ultrasonic sensor and the monitor signal from high-frequency power supplies 18 and 21 are used, but separate signals together with the monitor signal or without using the monitor signal, for example, monitor signals from a current value monitor measuring a current value flowing into the electrode plate for adsorption of the susceptor or wafer W, a reflected wave monitor measuring a reflected wave of the high-frequency power from the susceptor, and a phase monitor measuring a phase change of the high-frequency power, may also be used.

In the above exemplary embodiments, the case where the abnormality detection system is applied to the etching apparatus which is one of the plasma processing apparatuses is described, but the abnormality detection system may also be applied to another plasma processing apparatus such as a CVD film-forming apparatus, an ashing apparatus or the like, and further, the abnormality detection system is not limited to plasma processing apparatuses, and may also be applied to a coating-developing apparatus, a substrate cleansing apparatus, a heat-treatment apparatus, an etching apparatus or the like.

In the above exemplary embodiments, wafer W is used as the processed substrate, but the processed substrate is not limited thereto and may be a glass substrate such as a flat panel display (FPD) or the like.

The invention claimed is:

1. An abnormality detection system of detecting abnormality occurring in a processing apparatus in which acoustic emission (AE) as noise may be mixed into AE generated from an abnormality detection target, characterized by comprising:
   a plurality of ultrasonic sensors for detecting acoustic emission generated in the processing apparatus;
   a distributing unit configured to distribute each output signal of the plurality of ultrasonic sensors to a first signal and a second signal;
   a trigger generating unit configured to generate a trigger signal when a predetermined feature is detected by sampling the first signal at a first frequency;
   a trigger generation time determining unit configured to determine a trigger generation time by receiving the trigger signal;
   a data making unit configured to make sampling data by sampling the second signal at a second frequency higher than the first frequency; and
   a data processing unit configured to analyze the abnormality occurring in the processing apparatus by performing a waveform analysis of data corresponding to a predetermined period based on the trigger generation time determined by the trigger generation time determining unit among the sampling data.

2. The abnormality detection system of claim 1, characterized by further comprising:
   a trigger signal processing unit configured to integrate the plurality of trigger signals into one signal as a representative trigger signal when the plurality of trigger signals are generated within a predetermined period,
   wherein the trigger generation time determining unit determines the trigger generation time for the representative trigger signal.

3. The abnormality detection system of claim 1, characterized by further comprising:
   a filter configured to remove noise from each output signal of the plurality of ultrasonic sensors.

4. The abnormality detection system of claim 1, characterized in that the first frequency is 10 kHz to 5 MHz, and the second frequency is 500 kHz to 5 MHz.

5. The abnormality detection system of claim 1, wherein the processing apparatus is a processing apparatus for semiconductor wafers or glass substrates.

6. The abnormality detection system of claim 1, wherein the processing apparatus is any one of an etching apparatus, a CVD film forming apparatus, an ashing apparatus, a coating and developing apparatus, a substrate cleaning apparatus, and a thermal processing apparatus.

7. The abnormality detection system of claim 1, wherein the processing apparatus is a plasma processing apparatus.

8. A substrate processing apparatus including the abnormality detection system of claim 1.

9. An abnormality detection method for detecting abnormality occurring in a processing apparatus in which acoustic emission (AE) as noise may be mixed into AE generated from an abnormality detection target, characterized by comprising steps of:
   detecting acoustic emission generated in the processing apparatus by a plurality of ultrasonic sensors;
   distributing each output signal from the plurality of ultrasonic sensors which is acquired in the step of detecting to a first signal and a second signal by a distributing unit;
   generating a trigger signal by a signal generating unit when a predetermined feature is detected by sampling the first signal at a first frequency by an A/D conversion unit;
   determining a trigger generation time of the trigger signal by a time counter unit by receiving the trigger signal;
   making sampling data by sampling the second signal at a second frequency higher than the first frequency by the A/D conversion unit; and
   processing data of analyzing the abnormality occurring in the processing apparatus by performing a waveform analysis of data corresponding to a predetermined period by a computer based on the trigger generation time determined in the step of determining a trigger generation time among the sampling data.

10. The abnormality detection method of claim 9, characterized by further comprising a step of:
    processing a trigger signal by integrating the plurality of trigger signals into one signal as a representative trigger signal when the plurality of trigger signals are generated within a predetermined period in the generating of the trigger signal,
    wherein in the step of determining a trigger generation time, the trigger generation time is determined for the representative trigger signal.

11. The abnormality detection method of claim 9, characterized by further comprising a step of:
    removing noise from the first signal and the second signal acquired in the step of distributing by a filter.

12. The abnormality detection method of claim 9, characterized in that the first frequency is 10 kHz to 5 MHz, and the second frequency is 500 kHz to 5 MHz.

13. The abnormality detection method of claim 9, characterized in that the step of processing data further comprises steps of:
    cutting the data corresponding to the predetermined period from the sampling data;
    a first extracting of extracting a waveform feature quantity from down sampling data when a meaningful waveform exists in a made down sampling data by performing down sampling according to a representative value with respect to the data cut in the step of cutting;
    a second extracting of extracting a waveform feature quantity from the data cut in the step of cutting with respect to an analysis target by estimating a time of the waveform feature quantity extracted in the step of the first extracting to narrow the analysis target of the data cut in the step of cutting; and
    judging the abnormality occurring in the processing apparatus by performing pattern recognition between the waveform feature quantity acquired in the step of the second extracting and a predetermined abnormal pattern recognition model.

14. The abnormality detection method of claim 9, characterized by further comprising a step of:
    acquiring a process condition of predetermined processing executed in the processing apparatus performed before the step of detecting,
    wherein the step of detecting is performed only for an executing period of the predetermined processing included in the process condition acquired in the step of acquiring a process condition.

15. A non-transitory computer-readable recording medium of storing a program for executing an abnormality detection method for detecting the abnormality occurring in a processing apparatus, in which acoustic emission as noise may be mixed into AE generated from an abnormality detection target, predetermined as an abnormality detection system controlled by a computer, wherein the abnormality detection method comprises steps of:
- detecting acoustic emission generated in the processing apparatus by a plurality of ultrasonic sensors;
- distributing each output signal from the plurality of ultrasonic sensors which is acquired in the step of detecting to a first signal and a second signal by a distributing unit;
- generating a trigger signal by a signal generating unit when a predetermined feature is detected by sampling the first signal at a first frequency by an A/D conversion unit;
- determining a trigger generation time of the trigger signal by a time counter unit by receiving the trigger signal;
- making sampling data by sampling the second signal at a second frequency higher than the first frequency by the A/D conversion unit; and
- processing data of analyzing the abnormality occurring in the processing apparatus by performing a waveform analysis of data corresponding to a predetermined period by a computer based on the trigger generation time determined in the step of determining a trigger generation time among the sampling data.

* * * * *